(12) United States Patent
Yang

(10) Patent No.: US 9,549,858 B2
(45) Date of Patent: Jan. 24, 2017

(54) ULTRA-THIN ABSORBENT ARTICLE

(76) Inventor: Ching-Yun Morris Yang, Princeton Junction, NJ (US)

(*) Notice: Subject to any disclaimer, the term of this patent is extended or adjusted under 35 U.S.C. 154(b) by 1027 days.

(21) Appl. No.: 12/683,260

(22) Filed: Jan. 6, 2010

(65) Prior Publication Data

US 2011/0166540 A1 Jul. 7, 2011

(51) Int. Cl.
*A61F 13/15* (2006.01)
*A61F 13/472* (2006.01)
*A61F 13/532* (2006.01)
*A61F 13/537* (2006.01)

(52) U.S. Cl.
CPC ....... *A61F 13/472* (2013.01); *A61F 13/15203* (2013.01); *A61F 13/5323* (2013.01); *A61F 13/53713* (2013.01); *A61F 13/53747* (2013.01); *A61F 2013/53721* (2013.01)

(58) Field of Classification Search
CPC ............... A61F 13/530131; A61F 13/560182; A61F 13/530233; A61F 13/530248; A61F 13/530481; A61F 13/530489; A61F 13/5307
USPC .................................. 604/358, 367, 385.01
See application file for complete search history.

(56) References Cited

U.S. PATENT DOCUMENTS

| | | |
|---|---|---|
| 3,670,731 A | 6/1972 | Harmon |
| 3,959,569 A | 5/1976 | Burkholder, Jr. |
| 3,971,373 A | 7/1976 | Braun |
| 4,055,180 A | 10/1977 | Karami |
| 4,232,674 A | 11/1980 | Melican |
| 4,260,443 A | 4/1981 | Lindsay et al. |
| 4,324,247 A * | 4/1982 | Aziz ............................ 604/371 |
| 4,360,021 A | 11/1982 | Stima |
| 4,392,908 A | 7/1983 | Dehnel |
| 4,429,001 A | 1/1984 | Kolpin et al. |
| 4,433,024 A | 2/1984 | Eian |
| 4,469,734 A | 9/1984 | Minto et al. |
| 4,578,068 A | 3/1986 | Kramer et al. |
| 4,610,678 A | 9/1986 | Weisman et al. |
| 4,675,209 A | 6/1987 | Pedigrew |
| 4,797,318 A | 1/1989 | Brooker et al. |
| 4,851,069 A | 7/1989 | Packard et al. |
| 5,030,314 A | 7/1991 | Lang |
| 5,139,841 A | 8/1992 | Makoui et al. |
| 5,143,680 A | 9/1992 | Molnar et al. |
| 5,389,202 A | 2/1995 | Everhart et al. |
| 5,436,066 A | 7/1995 | Chen |

(Continued)

FOREIGN PATENT DOCUMENTS

| | | |
|---|---|---|
| EP | 1013291 B1 | 8/2005 |
| EP | 1697057 B1 | 11/2007 |

(Continued)

OTHER PUBLICATIONS

Derwent abstract file to U.S. Pat. No. 3,753,944; Date: Aug. 1973; Country: United States; Author: Sirota.*

(Continued)

*Primary Examiner* — Bradley Philips
(74) *Attorney, Agent, or Firm* — Edgewell Personal Care Brands, LLC

(57) ABSTRACT

The present invention generally relates to sanitary absorbent articles and in particular to disposable feminine sanitary absorbent articles that are extremely thin, highly absorbent and have superior structural integrity properties.

44 Claims, 7 Drawing Sheets

(56) References Cited

U.S. PATENT DOCUMENTS

| | | | |
|---|---|---|---|
| 5,482,761 A | 1/1996 | Palumbo et al. | |
| 5,514,324 A * | 5/1996 | Bachar | 264/518 |
| 5,543,215 A | 8/1996 | Hansen et al. | |
| 5,562,646 A | 10/1996 | Goldman et al. | |
| 5,591,147 A * | 1/1997 | Couture-Dorschner et al. | 604/369 |
| 5,599,335 A | 2/1997 | Goldman et al. | |
| 5,722,967 A | 3/1998 | Coles | |
| 5,803,920 A | 9/1998 | Gilman | |
| 5,830,202 A | 11/1998 | Bogdanski et al. | |
| 5,843,267 A * | 12/1998 | Cashaw et al. | 156/324 |
| 5,853,867 A | 12/1998 | Harada et al. | |
| 5,863,288 A | 1/1999 | Baker | |
| 5,873,963 A | 2/1999 | Trombetta et al. | |
| 5,879,751 A | 3/1999 | Bogdanski | |
| 5,900,109 A | 5/1999 | Sanders et al. | |
| 5,919,178 A | 7/1999 | Widlund | |
| 5,944,706 A | 8/1999 | Palumbo et al. | |
| 5,971,153 A | 10/1999 | Bauer et al. | |
| 6,024,822 A | 2/2000 | Alper et al. | |
| 6,093,474 A | 7/2000 | Sironi | |
| 6,140,550 A * | 10/2000 | Beihoffer et al. | 604/366 |
| 6,273,978 B1 | 8/2001 | Tai | |
| 6,329,565 B1 | 12/2001 | Dutkiewicz et al. | |
| 6,376,011 B1 | 4/2002 | Reeves et al. | |
| 6,458,877 B1 | 10/2002 | Ahmed et al. | |
| 6,515,195 B1 * | 2/2003 | Lariviere et al. | 604/380 |
| 6,534,572 B1 * | 3/2003 | Ahmed et al. | 524/275 |
| 6,554,223 B1 | 4/2003 | Tiettmeyer et al. | |
| 6,569,274 B1 | 5/2003 | Makoui et al. | |
| 6,573,422 B1 * | 6/2003 | Rosenfeld et al. | 604/368 |
| 6,586,512 B1 | 7/2003 | Dukes et al. | |
| 6,642,430 B1 | 11/2003 | Busam et al. | |
| 6,710,225 B1 * | 3/2004 | Everett et al. | 604/378 |
| 6,730,387 B2 | 5/2004 | Rezai et al. | |
| 6,790,798 B1 | 9/2004 | Suzuki et al. | |
| 6,803,400 B1 | 10/2004 | Butterbach et al. | |
| 6,972,011 B2 | 12/2005 | Maeda et al. | |
| 7,049,000 B2 | 5/2006 | Fossum et al. | |
| 7,235,278 B2 | 6/2007 | Fung et al. | |
| 7,250,093 B2 | 7/2007 | Heider et al. | |
| 7,276,053 B1 | 10/2007 | Lariviere et al. | |
| 7,321,007 B2 | 1/2008 | Gagliardi et al. | |
| 7,351,287 B2 | 4/2008 | Fung et al. | |
| 7,566,329 B2 | 7/2009 | Rosenfeld et al. | |
| 7,938,813 B2 * | 5/2011 | Wang et al. | 604/385.101 |
| 2002/0007165 A1 | 1/2002 | Rosenfeld et al. | |
| 2002/0032421 A1 | 3/2002 | Scott et al. | |
| 2002/0090453 A1 | 7/2002 | Muthiah et al. | |
| 2002/0095127 A1 | 7/2002 | Fish et al. | |
| 2002/0102392 A1 | 8/2002 | Fish et al. | |
| 2002/0115969 A1 | 8/2002 | Maeda et al. | |
| 2002/0176964 A1 | 11/2002 | Koslow | |
| 2003/0018314 A1 * | 1/2003 | Nozaki | A61F 13/15203 604/385.101 |
| 2003/0025945 A1 | 2/2003 | Lasko | |
| 2003/0060112 A1 | 3/2003 | Rezai et al. | |
| 2003/0129915 A1 * | 7/2003 | Harriz | 442/417 |
| 2003/0132762 A1 * | 7/2003 | Delzer et al. | 324/663 |
| 2003/0134559 A1 | 7/2003 | Delzer et al. | |
| 2003/0135177 A1 * | 7/2003 | Baker | 604/368 |
| 2003/0195485 A1 | 10/2003 | Rangachari et al. | |
| 2003/0225382 A1 | 12/2003 | Tombult-Meyer et al. | |
| 2004/0019339 A1 | 1/2004 | Ranganathan et al. | |
| 2004/0065232 A1 | 4/2004 | Lykke | |
| 2004/0087923 A1 * | 5/2004 | Cole | 604/365 |
| 2004/0116014 A1 * | 6/2004 | Soerens et al. | 442/59 |
| 2004/0167486 A1 | 8/2004 | Busam et al. | |
| 2004/0193127 A1 | 9/2004 | Hansson et al. | |
| 2004/0209093 A1 | 10/2004 | Keuchel et al. | |
| 2004/0236294 A1 | 11/2004 | Drzewiecki et al. | |
| 2005/0037144 A1 | 2/2005 | Cesiro et al. | |
| 2005/0049565 A1 * | 3/2005 | Joseph et al. | 604/367 |
| 2005/0096616 A1 | 5/2005 | Arora et al. | |
| 2005/0096623 A1 * | 5/2005 | Nhan et al. | 604/385.22 |
| 2005/0101928 A1 * | 5/2005 | Beruda et al. | 604/367 |
| 2005/0130542 A1 | 6/2005 | Klein | |
| 2005/0165371 A1 | 7/2005 | Giacometti | |
| 2005/0186351 A1 * | 8/2005 | Fung et al. | 427/420 |
| 2005/0215962 A1 * | 9/2005 | Litvay et al. | 604/358 |
| 2005/0224200 A1 | 10/2005 | Bouchard et al. | |
| 2005/0233071 A1 | 10/2005 | Fung et al. | |
| 2006/0005919 A1 * | 1/2006 | Schewe et al. | 156/276 |
| 2006/0020250 A1 | 1/2006 | Chester et al. | |
| 2006/0024433 A1 | 2/2006 | Blessing et al. | |
| 2006/0058755 A1 | 3/2006 | Rosenfeld et al. | |
| 2006/0070701 A1 | 4/2006 | Kobayashi et al. | |
| 2006/0084935 A1 | 4/2006 | Junqueira et al. | |
| 2006/0142714 A1 * | 6/2006 | Jackson et al. | 604/364 |
| 2007/0039690 A1 | 2/2007 | Walsh et al. | |
| 2007/0049886 A1 | 3/2007 | Mosbacher | |
| 2007/0066754 A1 | 3/2007 | Loeker et al. | |
| 2007/0078420 A1 * | 4/2007 | Sugiyama et al. | 604/361 |
| 2007/0197987 A1 | 8/2007 | Tsang et al. | |
| 2007/0246147 A1 | 10/2007 | Venturino et al. | |
| 2007/0282291 A1 | 12/2007 | Cole et al. | |
| 2008/0027402 A1 | 1/2008 | Schmidt et al. | |
| 2008/0051485 A1 | 2/2008 | Frei et al. | |
| 2008/0065038 A1 * | 3/2008 | Sugiyama et al. | 604/385.04 |
| 2008/0115898 A1 | 5/2008 | Gelli et al. | |
| 2010/0036342 A1 * | 2/2010 | Carlucci | A61F 13/5323 604/370 |

FOREIGN PATENT DOCUMENTS

| | | |
|---|---|---|
| WO | 2007111873 | 10/2007 |
| WO | 2008114165 | 9/2008 |

OTHER PUBLICATIONS http://www.merriam-webster.com/dictionary/lattice; Feb. 18, 2016.*

International Search Report for corresponding PCT Application No. PCT/US2011/020183.

* cited by examiner

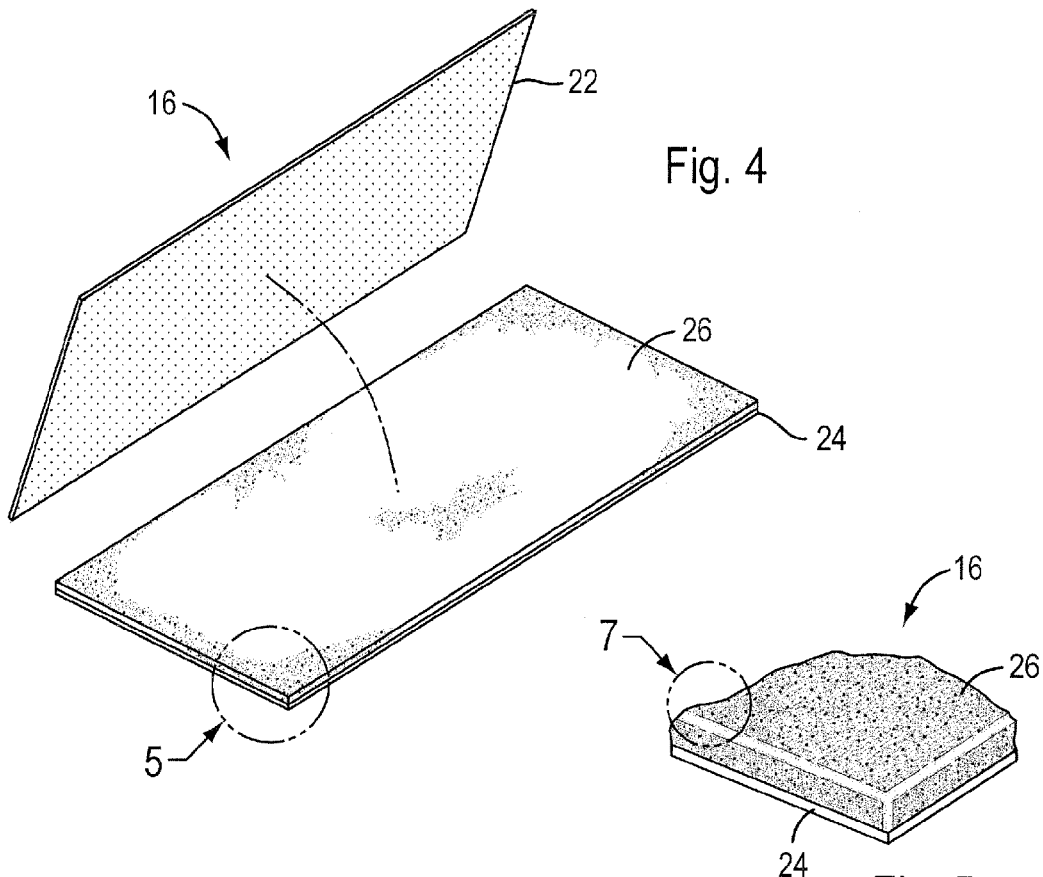
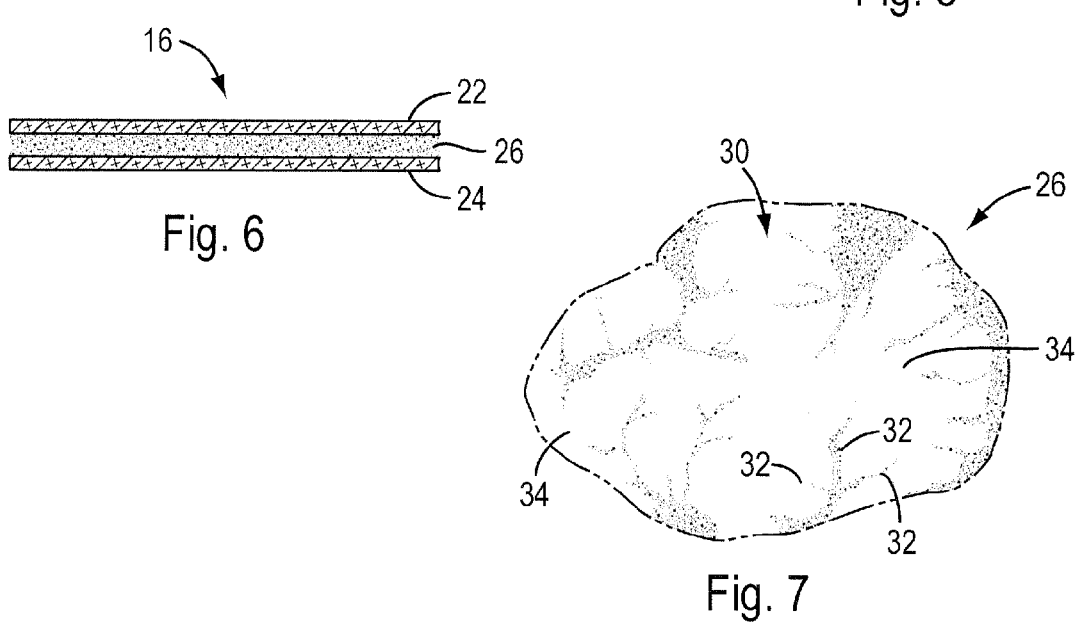

ULTRA-THIN ABSORBENT ARTICLE

FIELD OF THE INVENTION

The present invention generally relates to sanitary absorbent articles and in particular to disposable feminine sanitary absorbent articles that are extremely thin, highly absorbent and have superior structural integrity properties.

BACKGROUND OF THE INVENTION

Disposable absorbent articles, such as sanitary napkins, are well known in the art, and typically include a fluid pervious body facing cover layer, a liquid impermeable garment facing layer, and an absorbent core structure arranged between the cover layer and garment facing layer. Optionally, such articles may further include a transfer layer arranged between cover layer and the core.

Absorbent core structures used in disposable absorbent articles are typically made mainly of hydrophilic fibrous material such as cellulosic fibers. Such absorbent core structures may also include hydrogelling absorbent materials intermixed with such fibrous material to thereby increase the absorbent capacity of the core structure. Such hydrogelling absorbent materials are polymers that can absorb large quantities of liquid and thus are commonly known as "superabsorbent polymers" or "SAP".

The inventors of the present invention have discovered that conventional multi-layer core structures having a high superabsorbent polymer content typically have relatively poor structural integrity properties due to the fact that the superabsorbent polymer tends to prevent the effective bonding of the constituent core layers. This problem is further exacerbated when the absorbent core absorbs fluid because the superabsorbent polymer swells upon absorption of fluid thereby further reducing the structural integrity of the core structure. The relatively poor structural integrity of conventional core structures containing high levels of superabsorbent may cause absorbent articles containing such cores to structurally fail during manufacture or use.

Surprisingly, the absorbent core structures according to the present invention have a high degree of structural integrity despite containing high levels of superabsorbent polymer. Absorbent articles according to the present invention, including such inventive core structures, are extremely thin, highly absorbent and also retain a high level of structural integrity before and during use.

SUMMARY OF THE INVENTION

In view of the foregoing, the present invention provides, according to a first aspect of the invention, an absorbent article including a liquid permeable cover layer, a liquid impermeable barrier layer, an absorbent core arranged between the cover layer and barrier layer comprising a mixture of superabsorbent polymer and adhesive, wherein the superabsorbent polymer is present in an amount between about 50% to about 98% by weight and the adhesive is present in an amount between about 50% to about 2% by weight, wherein the mixture extends over a surface area of an adjacent layer in amount greater than 80% of a total surface area of the adjacent layer, wherein the mixture has a vertical layer delamination strength of greater than 9 N.

The present invention provides, according to a second aspect of the invention, an absorbent article including a liquid permeable cover layer, a liquid impermeable barrier layer, an absorbent core arranged between the cover layer and barrier layer comprising a mixture of superabsorbent polymer and adhesive, wherein the superabsorbent polymer is present in an amount between about 50% to about 98% by weight and the adhesive is present in an amount between about 50% to about 2% by weight, wherein the article has a thickness less than 3.0 mm, a fluid penetration time less than 40 seconds and a rewet less than 0.80 g, wherein the mixture has a vertical delaminating strength greater than 9 N.

In another aspect of the present invention, the present invention contemplates a method of making a laminate absorbent structure, comprising the steps of providing a first moving substrate comprising cellulosic fibrous material. The present method further contemplates providing a supply of adhesive material in the form of a curtain of adhesive fibers, and providing a supply of particulate absorbent material in the form of a curtain of particulate material. In accordance with the present invention, the curtain of particulate material is blended with the curtain of adhesive fibers, above the first moving substrate at a distance of no more than about 2.5 cm above the moving substrate to thus form a mixture of the particulate material and the adhesive fibers. The mixture is then deposited on the moving substrate, with the mixing of the adhesive fibers and the particulate material effected in closely spaced relationship above the moving substrate in order to promote the uniformity of the application of the mixture of adhesive and particulate material on the moving substrate.

After the mixture is deposited on the moving substrate, a second substrate comprising another cellulosic fibrous web is provided, and the second substrate placed on top of the mixture that was deposited on the first substrate, thereby forming a laminate. Formation is completed by applying pressure to the laminate, thereby achieving a second compaction resulting in improved bonding and whereby the adhesive fibers bond the particulate material to the first and second substrates while bonding the substrates to each other to form the laminate absorbent structure.

In a further aspect of the invention, the laminate absorbent structure is packaged by one of rolling and festooning, whereby the packaged laminate absorbent structure exhibits a package density greater than a density of the laminate absorbent structure. The ratio of the package density to the density of the laminate absorbent material is between about 1.7 and 5.0.

Other features and advantages of the present invention will become readily apparent from the following detailed description, the accompanying drawings, and the appended claims.

BRIEF DESCRIPTION OF THE DRAWINGS

Examples of embodiments of the present invention will now be described with reference to the drawings, in which:

FIG. 4 is a partially exploded view of the of the core structure of the absorbent article shown in FIG. 1;

FIG. 5 is an enlarged detailed view of that portion of the core structure encircled in FIG. 4;

FIG. 6 is a sectional view taken along line 6-6 in FIG. 2;

FIG. 7 is a detailed schematic view depicting the adhesive and superabsorbent mixture of that portion of the core structure encircled in FIG. 5.

DETAILED DESCRIPTION OF THE INVENTION

The present invention generally relates to disposable absorbent articles such as sanitary napkins, pantiliners, absorbent products for incontinence, and other disposable absorbent articles worn close to a wearer's body. Although the invention will be described herein with reference to a sanitary napkin 10, the invention may be utilized with other disposable sanitary absorbent articles and the like.

Figure 1:
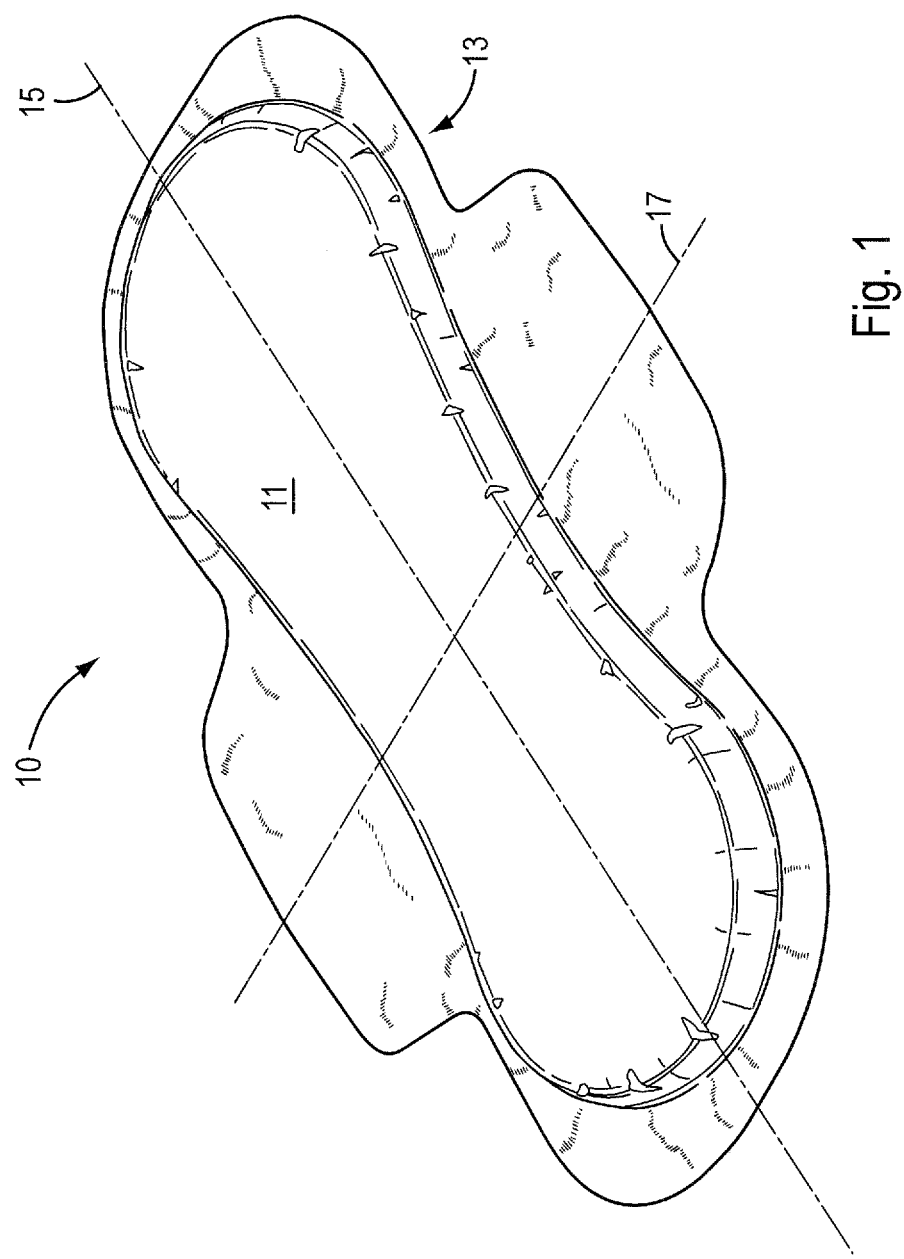
FIG. 1 is a perspective view of an absorbent article according to the present invention.

As shown in FIG. 1, the present invention, according to one embodiment of the invention, relates to a sanitary napkin 10 for absorbing bodily fluids. The sanitary napkin 10 includes a body facing surface 11, a garment facing surface 13, a longitudinally extending centerline 15, and a transversely extending centerline 17.

Figure 2:
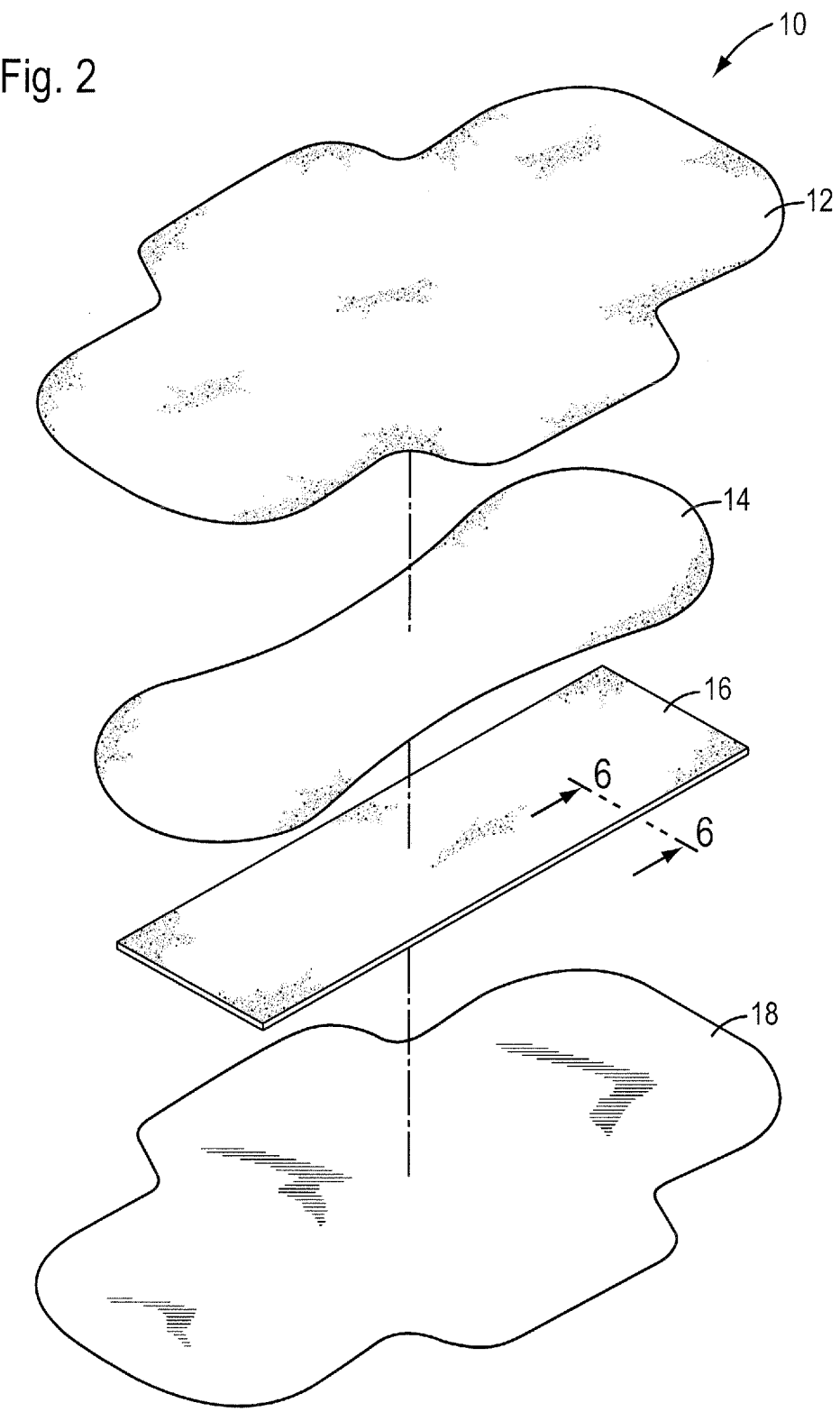
FIG. 2 is an exploded view of the absorbent article shown in FIG. 1, according to a first embodiment of the invention.
Figure 3:
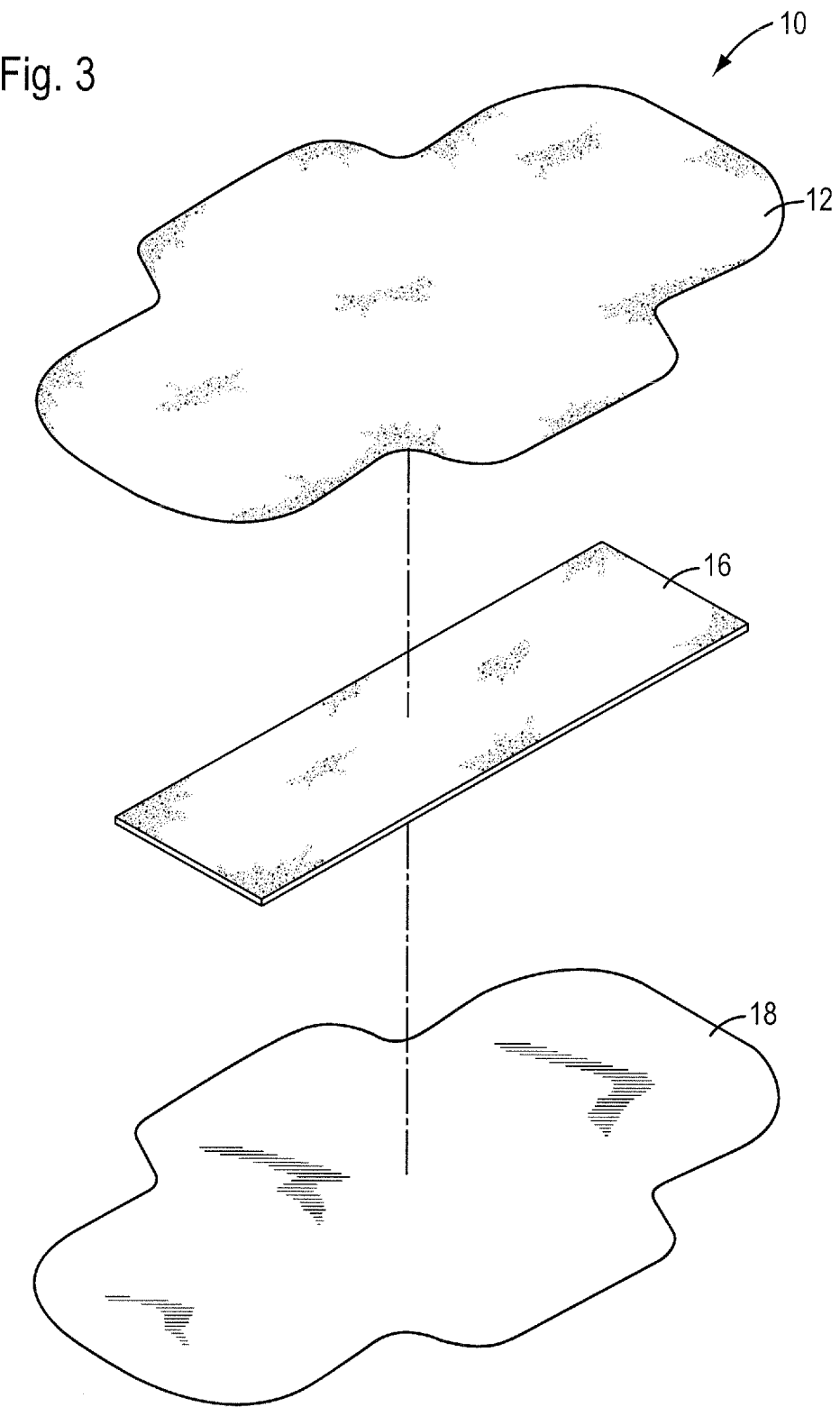
FIG. 3 is an exploded view of the absorbent article shown in FIG. 1, according to a second embodiment of the invention.

As best seen in the exploded view shown in FIG. 2, the sanitary napkin 10 includes, according to a first embodiment of the invention, a fluid permeable cover layer 12, an absorbent core structure 16, a transfer layer 14 arranged between the cover layer 12 and the absorbent core structure 16, and a fluid impermeable barrier layer 18. As best seen in the exploded view shown in FIG. 3, the sanitary napkin 10 includes, according to a second embodiment of the invention the cover layer 12, the absorbent core structure 16, and the fluid impermeable barrier layer 18, i.e. the transfer layer 14 is omitted.

Cover Layer

The cover layer 12 may be a relatively low density, bulky, high-loft non-woven web material. The cover layer 12 may be composed of only one type of fiber, such as polyester or polypropylene or it may include a mixture of more than one fiber. The cover may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Preferably, the cover layer 12 has a basis weight in the range of about 10 gsm to about 75 gsm.

Bi-component fibers may be made up of a polyester layer and a polyethylene sheath. The use of appropriate bi-component materials results in a fusible non-woven fabric. Examples of such fusible fabrics are described in U.S. Pat. No. 4,555,430 issued Nov. 26, 1985 to Chicopee. Using a fusible fabric increases the ease with which the cover layer may be mounted to the underlying absorbent layers and/or to the barrier layer.

The cover layer 12 preferably has a relatively high degree of wettability, although the individual fibers comprising the cover may not be particularly hydrophilic. The cover material should also contain a great number of relatively large pores. This is because the cover layer 12 is intended to take-up body fluid rapidly and transport it away from the body and the point of deposition. Therefore, the cover layer contributes little to the time taken for the napkin to absorb a given quantity of liquid (penetration time).

Advantageously, the fibers which make up the cover layer 12 should not lose their physical properties when they are wetted, in other words they should not collapse or lose their resiliency when subjected to water or body fluid. The cover layer 12 may be treated to allow fluid to pass through it readily. The cover layer 12 also functions to transfer the fluid quickly to the underlying absorbent layers of the article. Thus, the cover layer 12 is advantageously wettable, hydrophilic and porous. When composed of synthetic hydrophobic fibers such as polyester or bi-component fibers, the cover layer 12 may be produced with fiber containing hydrophilic finish or treated with a surfactant to impart the desired degree of wettability.

Alternatively, the cover layer 12 can also be made of polymer film having large pores. Because of such high porosity, the film accomplishes the function of quickly transferring body fluid to the inner layers of the absorbent system. Apertured co-extruded films such as those described in U.S. Pat. No. 4,690,679 can be used as a cover layer in articles according to the present invention.

The cover layer 12 may be embossed to the underlying absorbent system of the article in order to aid in promoting hydrophilicity by fusing the cover to the underlying absorbent layer. Such fusion may be effected locally, at a plurality of sites or over the entire contact surface of the cover layer and the absorbent system. Alternatively, the cover layer 12 may be attached to the absorbent system by other means such as by adhesion.

In one specific embodiment of the invention, the cover layer 12 is a 50 gsm (g/m$^2$) spunlace material including 70% polyester fibers by weight and 30% polypropylene fibers by weight. Suitable commercially available polyester fibers include Reliance PET 298G from Reliance Fibers Ltd., Mumbai, India or PET SN26530W3 from Far Eastern Textile Ltd., Taipei, Taiwan. A suitable commercially available polypropylene fiber is FV Hywettabie T135, wettable polypropylene fibers from ES Fibervisions, Inc., Athens, Ga.

Transfer Layer

Adjacent to the cover layer 12 on its inner side and bonded to the cover layer 12 is an optional transfer layer 14. The transfer layer 14 provides the means of receiving body fluid from the cover layer 12 and holding it until the underlying absorbent core structure 16 has an opportunity to absorb the fluid.

The transfer layer 14 preferably contains large pores with large voids that enables the layer to quickly absorb large quantities of fluid and hold it away from the outer side of the cover layer 12, thereby preventing the fluid from re-wetting the cover layer 12 and its surface. In this way the transfer layer 14 functions to quickly absorb fluid and then transmit the fluid to the underlying absorbent core structure 16.

The optional transfer layer 14 may be composed of fibrous materials, such as wood pulp, polyester, rayon, flexible foam, or the like, or combinations thereof. The transfer layer 14 may also comprise thermoplastic fibers for the purpose of stabilizing the layer and maintaining its structural integrity. The transfer layer 14 may be treated with surfactant on one or both sides in order to increase its wettability, although generally the transfer layer 14 is relatively hydrophilic and may not require treatment. The transfer layer 14 is preferably bonded on both sides to the adjacent layers, i.e. the cover layer 12 and the underlying absorbent core structure 16.

In one specific embodiment of the invention the transfer layer 14 is a 45 gsm through air bonded material including 40% by weight 5.0 denier polypropylene/polyethylene bicomponent fibers and 60% by weight 2.0 denier polypropylene/polyethylene bicomponent fibers.

Another suitable transfer layer 14 is a 45 gsm through air bonded material including 60% 2.2 dtex polypropylene/polyethylene bicomponent fibers and 40% 6.7 dtex polypropylene fibers, commercially available from Shalag Industries, Upper Galilee, Israel, under product code STA1PBL45.

Absorbent Core

As best seen in FIGS. 4-6, the absorbent core structure 16 according to the present invention is a multi-layer core construction including a first substrate layer 22, second substrate layer 24, and a mixture 26 of superabsorbent polymer and adhesive arranged between the substrate layers 22, 24. A preferred method for making the absorbent core structure 16 is described below herein under the section "Method for Making the Absorbent Core Structure".

Preferably the mixture 26 includes between about 50% to about 98% superabsorbent by weight and between about 50% to about 2% adhesive by weight. Despite the high amount of superabsorbent present in core structures according to the present invention, such core structures surprisingly possess superior structural integrity properties. For the purposes of the present invention, the term, "superabsorbent" or "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates.

In one specific embodiment of the invention each of the substrate layers 22 and 24 are formed from tissue, and in particular, 3207 from Cellu Tissue in East Hartford, Conn. Another suitable commercially available tissue material is Little Rapids type 2004 wetlaid tissue commercially available from Little Rapids Corp., Green Bay, Wis.

Preferred superabsorbents for use in the present invention include Sumitomo BA40B and Sumitomo SA70, commercially available from Sumitomo Seika Chemicals Co., Ltd., Osaka, Japan.

Preferably a hot melt adhesive is utilized as the adhesive in the mixture 26. A particularly suitable adhesive is HB Fuller NW1023 hot melt adhesive, commercially available from HB Fuller Company, St. Paul, Minn.

The mixture 26 preferably extends over a surface area that is greater than 80%, more preferably greater than 90%, and most preferably over 100% of the surface area of the adjacent layer to which the mixture 26 is applied. With reference the embodiment of the invention shown in FIG. 4, the mixture 26 is applied to substrate layer 24 and extends over 100% of the surface area of substrate layer 24. In those instances where the mixture 26 is applied between two differently sized directly adjacent substrate layers, the surface area of the smaller of two substrate layers should be used in determining the above described percentage.

The mixture 26 is preferably free of any fibrous material, such as cellulosic or synthetic fibrous material. In preferred embodiments of the present invention, the mixture 26 is composed entirely from superabsorbent polymer and adhesive.

As best seen in FIG. 4, the mixture 26 is preferably applied over the substrate layer 24 in a continuous layer, that is the mixture 26 is applied to the substrate layer 24 such that there are no discontinuous zones or areas where the mixture 26 is not present. Preferably the mixture 26 is applied such that it extends over an area greater than 2500 $mm^2$, and more preferably over an area in the range of between 3000 $mm^2$ and 15000 $mm^2$. The mixture 26 is preferably applied to the substrate layer 24 in an add on amount between about 5 gsm ($g/m^2$) and about 150 gsm ($g/m^2$).

As best seen in FIG. 7, the adhesive that forms part of the mixture 26 forms a three dimensional lattice structure 30 that is formed from a plurality of interconnected lattice segments 32. Each of the lattice segments 32 preferably has a diameter in the range of about 0.02 mm and about 0.08 mm. The diameter of such lattice segments 32 can be measured utilizing a conventional microscopic techniques known to those of skill in the art. As seen in FIG. 7, the superabsorbent particulate material 34 is suspended within the matrix defined by the three dimensional lattice structure 30.

Absorbent core structures 16 according to the present invention preferably have a thickness of less than 1.5 mm, more preferably less than 1.2 mm and most preferably less than 1.0 mm.

In one specific embodiment of the invention, the absorbent core structure 16 includes a first 17 gsm wetlaid tissue layer (commercially available as Little Rapids type 2004 wetlaid tissue, Little Rapids Corp., Green Bay, Wis.), a second 17 gsm wetlaid tissue layer (commercially available as type 3207 from Cellu Tissue, East Hartford, Conn.), an adhesive/superabsorbent mixture including 80 gsm superabsorbent (Sumitomo SA70, commercially available from Sumitomo Seika Chemicals Co., Ltd., Osaka, Japan) and 6 gsm hotmelt adhesive (HB Fuller NW1023 hot melt adhesive, commercially available from HB Fuller Company, St. Paul, Minn.), the adhesive/superabsorbent mixture being arranged between the two tissue layers such that mixture extends continuously over 100% of the surface area of the two identically sized tissue layers In another specific embodiment of the invention, the absorbent core structure 16 includes a first 17 gsm wetlaid tissue layer (commercially available as Little Rapids type 2004 wetlaid tissue, Little Rapids Corp., Green Bay, Wis.), a second 17 gsm wetlaid tissue layer (commercially available as type 3207 from Cellu Tissue, East Hartford, Conn.), an adhesive/superabsorbent mixture including 20 gsm superabsorbent (Sumitomo SA70, commercially available from Sumitomo Seika Chemicals Co., Ltd., Osaka, Japan) and 3 gsm hotmelt adhesive (HB Fuller NW1023 hot melt adhesive, commercially available from HB Fuller Company, St. Paul, Minn.), the adhesive/superabsorbent mixture being arranged between the two tissue layers such that mixture extends continuously over 100% of the surface area of the two identically sized tissue layers.

In manufacturing the absorbent feminine hygiene product associated with the present invention, it is advantageous to receive the core material in the form of a pre-made package. In this way, the manufacturing process associated with making the core is separated from the converting line as the two processes have different run parameters. These packages can take the form of slit rolls, festooned boxes, or spooled rolls. There is a significant advantage to making the package as dense as possible for two reasons. First, the shipping costs can be reduced when the size of the package is smaller. Second, the available number of lineal meters in a package of a given size is increased, which reduces the frequency of needing to make splices to a new package when one runs out. While the practice of splicing on high-speed converting equipment is well known by those skilled in the art, there are inefficiencies that result from missed splices, as well the handling time associated with executing splices. Additionally, the products containing the splice frequently need to be culled, producing line scrap.

An unexpected discovery in working with the core material of the present invention was that the Vertical Delamination Strength increased after storage in the package. It was also unexpectedly found that the density of the material in the package was significantly higher than the density of the material after it was removed from the package. Combining this property with the fact that the material is very thin, the result is packages that contain an unexpectedly high number of lineal meters of material. It is useful to establish some definitions with which to describe these findings:

Caliper (of the Material):

A 0.075 m×0.3 m material sample is placed in an Emveco Model 200A microgage with a foot pressure of 0.0725 psi and diameter of 2.2-inches and the machine is cycled to measure and store caliper readings in millimeters in 6 locations on the sample. The average caliper is reported using the average function of the Emveco.

Density (of the Material):

A material sample 75 mm×300 mm is weighed on a lab balance, and the caliper is measured as described above in millimeters.

$$\text{Basis Weight(gsm)}=\text{Sample Weight(g)Sample Area (m}^2)=\text{Sample Weight(g)}/(0.075\text{m}\times0.3\text{m})$$

$$\text{Density(g/cc)}=\text{Basis Wt(gsm)}/(\text{Caliper(mm)}\times1000)$$

Wind Layer Thickness (on a Roll):

This is the calculated thickness of a single layer of material wound in the roll. The area of the circular face of the roll is equal to the area of the slit edge of the material that comprises that face. The area of the donut-shaped roll face can be approximated by the area of a circle the diameter of the roll minus the area of a second circle the diameter of the core. The area of each successive wind edge that makes up the roll face can be approximated by multiplying the length of the material in that wind by its wound thickness. The area of each successive wind is then added together to yield the total. Both approximations become precise as the thickness of the wind layer being considered is small and they are sufficient for this definition.

The following equations are used:

$$\text{Roll Face Area(m}^2)=((\pi/4)\times\text{Roll Diameter}^2)-((\pi/4)\times\text{Core Diameter}^2)$$

$$\text{Wind Layer Thickness(mm)}=1000(\text{mm/m})\times(\text{Roll Face Area(m}^2))/(\text{Length of Material on Roll (m)})$$

Material Density (in the roll)

$$\text{Material Density in the roll}=(\text{Material Basis Weight (gsm)})/(\text{Wind Layer Thickness(mm)}\times1000)$$

Density Ratio:

$$\text{Density Ratio}=(\text{Material Density in the roll(g/cc)})/(\text{Density of the material off of the roll(g/cc)}).$$

Also:

$$\text{Density Ratio}=(\text{Caliper of the material off of the roll(mm)})/(\text{Wind Layer Thickness on the roll. (mm)})$$

Density Ratio for a Festoon Box:

Given the material length in the box, the inside dimensions of the box, the depth of the material fill in the box, and the representative basis weight of the material in the box, the Density Ratio for a festooned package of material can be calculated as follows:

$$\text{Material Weight in box(g)}=(\text{Material Length in box (m)})\times(\text{Slit Width(m)})\times(\text{Average Basis Weight (gsm)})$$

$$\text{Packed Density in Box(g/cc)}=(\text{Material Weight in box(g)})/((\text{Box Length(cm)})\times(\text{Box Width(cm)})\times(\text{Material Fill Depth(cm)}))$$

$$\text{Density Ratio}=\text{Density of Material(g/cc)}/\text{Packed Density in Box(g/cc)}$$

Thirty-five (35) rolls of Material Example 1 of absorbent core described above were produced at a diameter of 1075 mm. The number of lineal meters of material on each roll was recorded from the slitter readout. The Wind Layer Thickness was calculated according to the formula above for each roll and the Caliper of a sample of material taken from each roll was measured and recorded. The average values for the rolls are recorded in table 1 below:

TABLE 1

| Average Roll Diameter (mm) | Average Wind Layer Thickness (mm) | Average material Caliper removed from roll (mm) | Density Ratio |
|---|---|---|---|
| 1075 | 0.239 | 0.851 | 3.2 |

The average Material Density in the roll was 3.2 times the Density of the material separate from the roll.

Twenty-nine (29) rolls of Material Example 2 of the absorbent core described above were made and wound to a diameter of 1075 mm. The lineal meters of material on each roll was recorded from the slitter readout. The Wind Layer Thickness was calculated according to the formula above for each roll and the Caliper of a sample of material taken from each roll was measured and recorded. The average values for the rolls are recorded in table 2 below.

TABLE 2

| Average Roll Diameter (mm) | Average Wind Layer Thickness (mm) | Average Material Caliper removed from roll (mm) | Density Ratio |
|---|---|---|---|
| 1075 | 0.145 | 0.721 | 5.0 |

The average Material Density on the rolls was 5 times the average Density of the material separate from the rolls.

Material according to Material Example 1 of the absorbent core described above was made into rolls and then run into 7 festoon boxes using a Santex model CH9555 Tobel festooner. The festoon box had inside dimensions of 92 cm×114 cm×95 cm depth. The average Packed Density of the material in the box was calculated as was the average Density of material samples taken from the rolls before they were festooned. These values are recorded in Table 3 below along with the Density Ratio taken from these average values:

TABLE 3

| Average Packed Density in Box (g/cc) | Average Material Density prior to festooning (g/cc) | Density Ratio |
|---|---|---|
| 0.25 | 0.15 | 1.7 |

The average Packed Density of the material in the festoon box was 1.7 times higher than the Density of the material separate from the box.

It was further unexpectedly found that the Density of the material after it was removed from the roll was very similar to that of the material before it was made into a roll. A sample made according to Material Example 1 had a Density of 0.14 g/cc before it was rolled. The material was stored for 4-months on the roll and when removed from the roll another sample was measured and the Density was still at 0.14 g/cc. The result indicates that the apparent density before and after the wind are very similar and the SAP particles are not crushed in the rolls.

To further understand the nature of the high Density Ratios, a roll containing 1000 lineal meters of material was produced according to Material Example 1. The roll was allowed to equilibrate for a time period greater than 3-days. After cutting away a slab of approximately an inch of total Wind Thickness of material from the outside of the roll, a slab of material was removed containing 9-plies of material. The slab was carefully cut into segments 120 mm in length being careful to keep the nested layers in the segments fully engaged with one another. The Caliper of the slab was measured and then the plies were separated and the Caliper of each of the plies was measured using an Emveco Model 200A Migrogage. The Caliper of each slab, and the sum of the Calipers of the separated plies taken from each slab were obtained. Then the sum of the Calipers of the plies was divided by the Caliper of the slab to yield a Caliper Ratio. These are reported in table 4 below:

TABLE 4

| | Slab Caliper (mm) | Sum of Calipers of all 9 Plies (mm) | Caliper Ratio (Sum of Plies/Slab) |
|---|---|---|---|
| Slab 1 | 3.32 | 7.50 | 2.26 |
| Slab 2 | 3.36 | 7.54 | 2.25 |
| Slab 3 | 3.29 | 9.52 | 2.90 |

Because the Basis Weight does not change when the plies are removed from the slab, the Caliper Ratio is also the average Density Ratio between the engaged slab and the separate plies. Without any pressure being maintained, the slabs had Densities more than 2.2 times that of the average Density of the individual plies after they are removed.

Without being bound by any particular theory, it is believed that under packing pressure, the core material is reshaped to generate maximum engagement that allows the pressure sensitive adhesive lattice to reach its maximum bonding function. The layers in the packages are very rough in surface structure and the rough surfaces reshape themselves when held in contact with one another under the pressure of the package to nest together in the package. It is believed that the pressure sensitive adhesive lattice forms new bonds and the surface assumes the nested shape over time which allows the surfaces to remain engaged and the higher package densities are for the most part maintained without applied pressure after the re-shaping takes place.

Based on the Density Ratios seen, the theory above would suggest that a protrusion on one layer in the package may protrude through the plane of as many as two or even more adjacent layers. Again, without being bound by any particular theory, it is thought that the wind pressure of the roll is pressing the relatively rigid particulate towards a more closely packed state, and the very compliant substrate that contains the particulate simply conforms to the new particle positions. It is believed that a Density Ration as high as about 7 can be achieved, desired.

This behavior is not believed to be a function of the type of material that comprises the particulate and the scope of this invention would not be limited only to materials that contain superabsorbent polymer.

Figure 9:
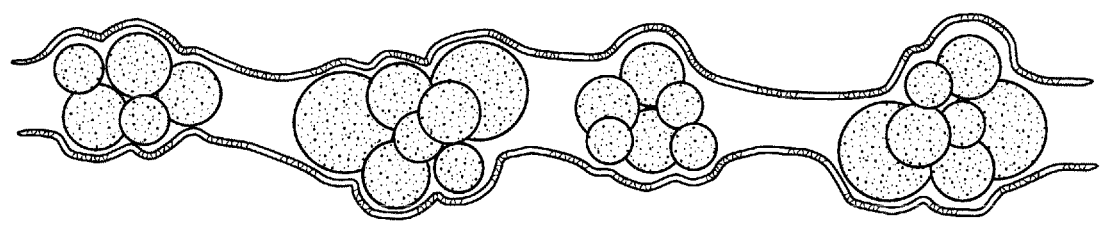
FIGS. 9 and 10 are diagrammatic sectional views of the laminate formed in accordance with the present invention; showing the effect of the secondary compaction.
Figure 10:
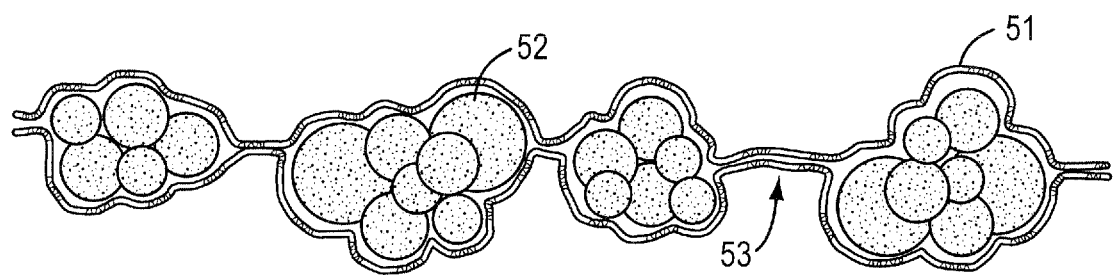

FIGS. 9 and 10 are diagrammatic views of the laminate formed in accordance with the present invention, which views illustrate the effect of the last step of the process in which the laminate material is formed into a package under pressure and stored. Both FIGS. 9 and 10 represent sectional views of the laminate, with particulate 52 represented as the clustered spheres of an aggregate-type SAP. The bottom tissue layer is shown at 53, and the top tissue layer is shown at 54. Adhesive fibers have been omitted for clarity. FIG. 10 shows the additional material surface roughness and bonding that is believed to take place after the material is stored in the package, which results in the cited increase in VDS from that process step.

Figure 11:
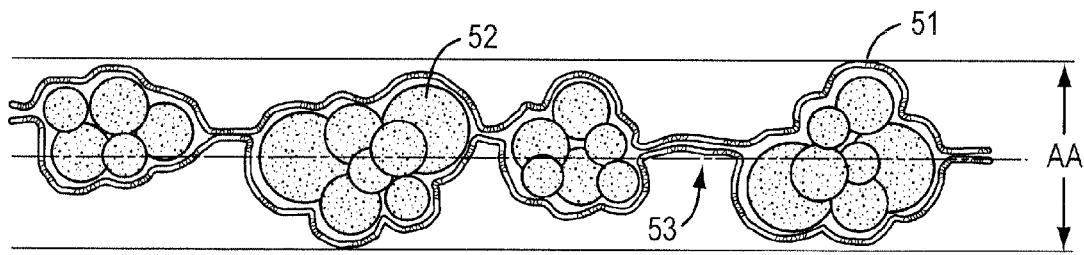
FIGS. 11, 12, and 13 are diagrammatic sectional views of the present laminate illustrating nesting of adjacent laminate layers attendant to packaging.
Figure 12:
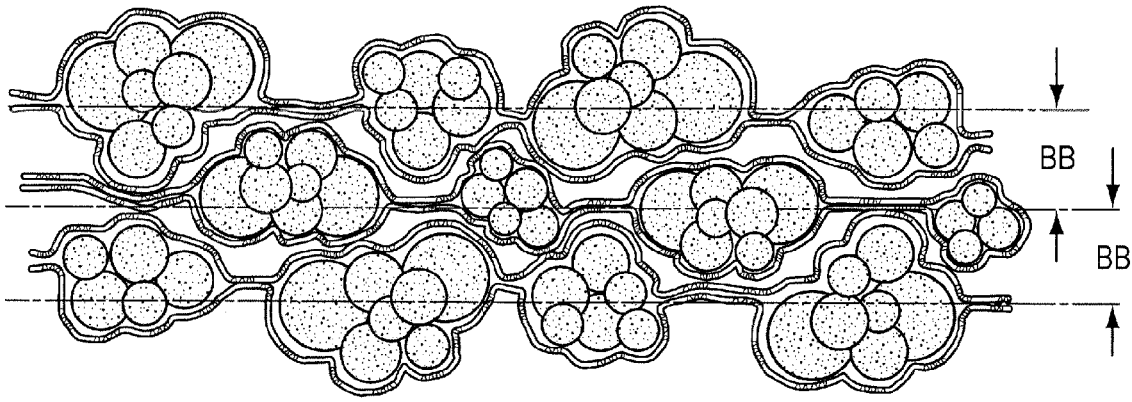
Figure 13:
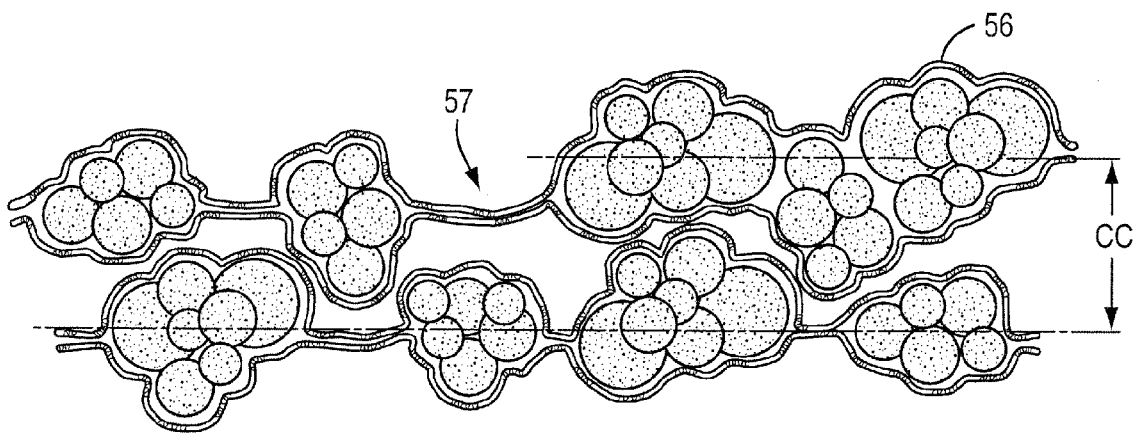

FIGS. 11, 12, and 13 are diagrammatic views of the laminate which illustrate the present belief of how the surface nesting would appear, with FIG. 11 being a sectional view of a single ply of the laminate of material, exhibiting a caliper AA. FIG. 12 represents a sectional view representing 3 plies of laminate in a package of wind layer thickness BB, which is less than AA, showing the nesting effect which is believed to be achieved by practice of the present invention. FIG. 13 illustrates the importance of the features of the present process that generate and promote uniformity in the distribution of particulate, showing a sectional view representing 2 plies of laminate in a package, in which one laminate layer contains a region 56 of higher SAP basis weight, which causes the wind layer thickness CC to be thicker than BB. It also creates an adjacent low-density region 57 in the roll. This effect would be most disruptive if the heavy region 56 were a heavy streak of particulate running in the machine direction.

Barrier Layer

Underlying the absorbent core 16 is a barrier layer 18 comprising liquid-impervious film material so as to prevent liquid that is entrapped in the absorbent system 16 from egressing the sanitary napkin and staining the wearer's undergarment. The barrier layer 18 is preferably made of polymeric film, although it may be made of liquid impervious, air-permeable material such as repellent-treated non-woven or micropore films or foams.

The barrier layer may be breathable, i.e., permits vapor to transpire. Known materials for this purpose include nonwoven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet. The cover layer 12 and the barrier layer 18 are joined along their marginal portions so as to form an enclosure or flange seal that maintains the absorbent core structure 16 captive. The joint may be made by means of adhesives, heat-bonding, ultrasonic bonding, radio frequency sealing, mechanical crimping, and the like and combinations thereof.

In one specific embodiment of the invention the barrier layer 18 is a polypropylene film material commercially available under product code XP3471A from Pliant Corporation, Schaumburg, Ill.

Absorbent articles of this invention may or may not include wings, flaps or tabs for securing the absorbent article to an undergarment. Wings, also called, among other things, flaps or tabs, and their use in sanitary protection articles are described in U.S. Pat. No. 4,687,478 to Van Tilburg; U.S. Pat. No. 4,589,876 also to Van Tilburg, U.S. Pat. No. 4,900,320 to McCoy, and U.S. Pat. No. 4,608,047 to Mattingly. The disclosures of these patents are incorporated herein by reference in their entirety. As disclosed in the above documents, wings are generally speaking flexible and configured to be folded over the edges of the underwear so that the wings are disposed between the edges of the underwear and the wearer.

The absorbent article of the present invention may be applied to the crotch by placing the garment-facing surface against the inside surface of the crotch of the garment. Various methods of attaching absorbent articles may be used. For example, chemical means, e.g., adhesive, and mechanical attachment means, e.g., clips, laces, ties, and interlocking devices, e.g., snaps, buttons, VELCRO (Velcro USA, Inc., Manchester, N.H.), zipper, and the like are examples of the various options available to the artisan.

Adhesive may include pressure sensitive adhesive that is applied as strips, swirls, or waves, and the like. As used herein, the term pressure-sensitive adhesive refers to any releasable adhesive or releasable tenacious means. Suitable adhesive compositions, include, for example, water-based pressure-sensitive adhesives such as acrylate adhesives. Alternatively, the adhesive composition may include adhesives based on the following: emulsion or solvent-borne adhesives of natural or synthetic polyisoprene, styrene-butadiene, or polyacrylate, vinyl acetate copolymer or combinations thereof; hot melt adhesives based on suitable block copoylmers—suitable block copolymers for use in the invention include linear or radial co-polymer structures having the formula (A–B)x wherein block A is a polyvinylarene block, block B is a poly(monoalkenyl) block, x denotes the number of polymeric arms, and wherein x is an integer greater than or equal to one. Suitable block A polyvinylarenes include, but are not limited to Polystyrene, Polyalpha-methylstyrene, Polyvinyltoluene, and combinations thereof. Suitable Block B poly(monoalkenyl) blocks include, but are not limited to conjugated diene elastomers such as for example polybutadiene or polyisoprene or hydrogenated elastomers such as ethylene butylene or ethylene propylene or polyisobutylene, or combinations thereof. Commercial examples of these types of block copolymers include Kraton™ elastomers from Shell Chemical Company, Vector™ elastomers from Dexco, Solprene™ from Enichem Elastomers and Stereon™ from Firestone Tire & Rubber Co.; hot melt adhesive based on olefin polymers and copolymers where in the olefin polymer is a terpolymer of ethylene and a co-monomers, such as vinyl acetate, acrylic acid, methacrylic acid, ethyl acrylate, methyl acrylate, n-butyl acrylate vinyl silane or maleic anhydride. Commercial examples of these types of polymers include Ateva (polymers from AT plastics), Nucrel (polymers from DuPont), Escor (from Exxon Chemical).

Where adhesive is used, a release strip may be applied to protect the adhesive on the absorbent article prior to attaching the absorbent article to the crotch. The release strip can be formed from any suitable sheet-like material adheres with sufficient tenacity to the adhesive to remain in place prior to use but which can be readily removed when the absorbent article is to be used. Optionally, a coating may be applied to release strip to improve the ease of removabilty of the release strip from the adhesive. Any coating capable of achieving this result may be used, e.g., silicone.

Any or all of the cover, transfer layer, absorbent core structure, barrier layer, and adhesive layers may be colored. Such coloring includes, but is not limited to, white, black, red, yellow, blue, orange, green, violet, and mixtures thereof. Color may be imparted according to the present invention through dying, pigmentation, and printing. Colorants used according the present invention include dyes and inorganic and organic pigments. The dyes include, but are not limited to, anthraquinone dyes (Solvent Red 111, Disperse Violet 1, Solvent Blue 56, and Solvent Green 3), Xanthene dyes (Solvent Green 4, Acid Red 52, Basic Red 1, and Solvent Orange 63), azine dyes (Jet black), and the like. Inorganic pigments include, but are not limited to, titanium dioxide (white), carbon black (black), iron oxides (red, yellow, and brown), chromium oxide (green), ferric ammonium ferrocyanide (blue), and the like.

Organic pigments include, but are not limited to diarylide yellow AAOA (Pigment Yellow 12), diarylide yellow AAOT (Pigment Yellow 14), phthalocyanine blue (Pigment Blue 15), lithol red (Pigment Red 49:1), Red Lake C (Pigment Red), and the like.

The absorbent article may include other known materials, layers, and additives, such as, foam, net-like material, perfumes, medicaments or pharmaceutical agents, moisturizers, odor control agents, and the like. The absorbent article can optionally be embossed with decorative designs.

The absorbent article may be packaged as unwrapped absorbent articles within a carton, box or bag. The consumer withdraws the ready-to-use article as needed. The absorbent article may also be individually packaged (each absorbent article encased within an overwrap).

Also contemplated by the present invention are asymmetrical and symmetrical absorbent articles having parallel longitudinal edges, dog bone- or peanut-shaped, as well as articles having a tapered construction for use with thong-style undergarments.

Method for Making the Absorbent Core Structure

Figure 8:
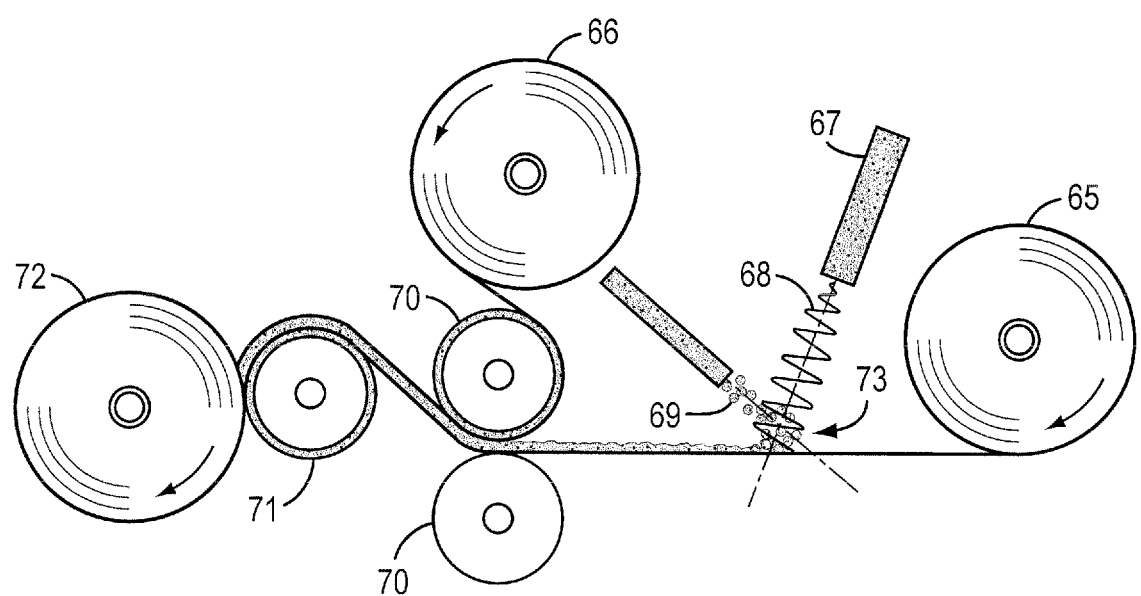
FIG. 8 schematically depicts an apparatus for making the absorbent core structure shown in FIGS. 4 and 5.

A preferred method for making the absorbent core structure 16 used in absorbent articles according to the present invention is described below with reference to FIG. 8.

The absorbent core structure is manufactured by first providing a continuous moving web of tissue substrate. The process is diagrammed in FIG. 8. The roll of tissue (at 57 in FIG. 8) is unwound and fed into the process at a fixed speed. Practice for unwinding rolls of material and feeding them into a process under a controlled manner are well known to those skilled in the art. Unwinding and splicing equipment are commercially available, and ideally should be designed to suit the roll size and process speeds.

A continuous curtain of hot melt adhesive fibers is extruded from a hot melt applicator 67, which is directed at the moving substrate. Adhesive fibers can be produced by first extruding melted adhesive from an evenly spaced row of orifices. Air jets then impinge on the streams of adhesive causing them to accelerate and wave or spiral. This stretches the adhesive into thin fibers, and the waving is designed to be wide enough that the adjacent fibers overlap with one another, and when deposited on a substrate create a mat of hot melt fibers with the goal being that the coverage is substantially uniform. Hot melt adhesive fiber application systems are commercially available, with a particularly desirable system being the Equity UFD head from ITW Dynatec in Hendersonville Tenn., along with an appropriately sized hot melt feed system to match the speed and processing parameters.

At an appropriate distance from the head, the fibers reach a point where they are at the desired degree of attenuation and they overlap to form the most uniform distribution of fiber. The moving tissue substrate 65 should be placed at that distance to have the hot melt fibers deposited onto the surface.

A flattened, uniform stream or curtain of particulate (69 in FIG. 8) is directed to intersect with the stream of hot melt fibers. Metering particulate is well known to those skilled in the art, such as various volumetric devices such as fixed-rate screw feeders, as well as a loss-in weight system where the feed hopper is set on a load cell, which controls the speed of the screw. Such systems are available from companies such as K-Tron or Acrison. The particulate can then be formed into a flat stream using various means, such as a vibratory feed, or simply an angled chute.

The particulate mixes with the hot melt fibers and is deposited onto the web. It is desirable that the fibers are sufficiently attenuated to produce fibers that are smaller in diameter than most of the particulate, as well as to produce enough fibers so that most of the particulate is captured by adhesive fibers within the defined mixing zone, and not allowed to tumble past the mixing zone and onto the web. Without being restricted by a particular set of theories, it is believed by the applicants that it is desirable to maximize the uniformity of the particle distribution on the surface of the substrate, avoiding clumping and streaking, which may create high, and low-particle basis weight regions on the surface, which might interfere with how the material surfaces nest together, as well as create non-uniformities in fluid handling properties. It has been found that if the region of mixing (73 in FIG. 8) is kept very close to the substrate, the uniformity is improved. Most desirably, the axes of the two streams or curtain should cross at a height about 1.0 centimeters above the substrate, understanding that each stream or curtain has a thickeners, and that the streams or curtains should be kept sufficiently flat so that most of the defined area where the streams mix is maintained at no more than about 2.5 centimeters above the substrate.

After applying the mix of particles and adhesive fibers to the first tissue layer, a second tissue layer is introduced from a roll 66 and combined with the first layer, forming a laminate comprising two layers of tissue with a layer of a mixture of particulate and adhesive fibers between them, with the adhesive fibers adhering to both the particulate and the two substrates, as well as each other, forming the lattice structure mentioned earlier. This laminate is pressed by a nip roll 70 with a pressure of approximately 0.5N per lineal centimeter with a rubber roll surface that is compliant enough that the caliper of the web is reduced by less than 5% upon passing through the nip. Particularly desirable is a roll surface formed from a 12 mm thick cover of sponge urethane rubber.

The web is then wound into a roll to form a package which can be supplied to the converting operation. A particularly advantageous winder is surface driven, using a driven drum 71 to drive the roll as it is being formed. This drum not only drives the material and the roll at the requisite surface speed, it also provides pressure at the nip with the roll to engage the surfaces of the adjacent layers within the roll causing them to nest. The package of material 72 is pressed against the drive roll 71 at a sufficient pressure to cause the roll density to reach a level at least 1.5 times that of the material when it is removed from the roll, and most desirably near a maximum possible value for the particular grade being run, but short of applying a pressure that destabilizes the roll or damages the material.

The material then is left in the package to equilibrate under the wind pressure. During this time, it is observed that the Vertical Delamination Strength increases significantly. A 1000 lineal meter roll was produced of the first specific embodiment, mentioned earlier, which had VDS value of around 3N immediately after winding, and after it was allowed to equilibrate for 72-hours, the VDS value was 14N. During this period, it is also observed that the interlocking nesting surfaces of the wound layers which allow the rolls to have a much higher density than the material after it is removed become permanently conformed to each other, and slabs of material comprising of multiple layers can be cut from the roll without greatly increasing the thickness of the nested layers as the roll pressure is released.

The material of the present invention can also be made into festooned packages, by any means and equipment well-known in the art. It is desirable that fill depth in the box be deep enough that the distributed weight of the material applies sufficient pressure to cause the package density to exceed that of the material after it is removed from the package by a factor of at least 1.5. Other wound packages such as spools can be formed in a similar manner as rolls as long as the internal pressure in the package is sufficient to cause the surfaces of the layers to nest as described above.

Procedure for Determining Modified Circular Bend Stiffness (MCB)

Absorbent articles according to the present invention are highly flexible, thereby providing enhanced comfort to the user. The Modified Circular Bend Stiffness (MCB) test method set forth below is designed to measure the multi-directional flexibility of an absorbent article. Absorbent articles according to the present invention preferably have an MCB stiffness of less than 150 g, more preferably less than 100 g, and most preferably less than 50 g.

Modified Circular Bend Stiffness (MCB) is determined by a test that is modeled after the ASTM D 4032-82 CIRCULAR BEND PROCEDURE, the procedure being considerably modified and performed as follows. The CIRCULAR BEND PROCEDURE is a simultaneous multi-directional deformation of a material in which one face of a specimen becomes concave and the other face becomes convex. The CIRCULAR BEND PROCEDURE gives a force value related to flexural resistance, simultaneously averaging stiffness in all directions.

The apparatus necessary for the CIRCULAR BEND PROCEDURE is a modified Circular Bend Stiffness Tester, having the following parts:

1. A smooth-polished steel plate platform, which is 102.0 mm by 102.0 mm by 6.35 mm having an 18.75 mm diameter orifice. The lap edge of the orifice should be at a 45 degree angle to a depth of 4.75 mm;

2. A plunger having an overall length of 72.2 mm, a diameter of 6.25 mm, a ball nose having a radius of 2.97 mm and a needle-point extending 0.88 mm therefrom having a 0.33 mm base diameter and a point having a radius of less than 0.5 mm, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), than the needle-point should not be used. The bottom of the plunger should be set well above the top of the orifice plate. From this position, the downward stroke of the ball nose is to the exact bottom of the plate orifice;

3. A force-measurement gauge and more specifically an Instron inverted compression load cell. The load cell has a load range of from about 0.0 to about 2000.0 g;

4. An actuator and more specifically the Instron Model No. 1122 having an inverted compression load cell. The Instron 1122 is made by the Instron Engineering Corporation, Canton, Mass.

In order to perform the procedure for this test, as explained below, three representative product samples for each article to be tested are necessary. The location of the sanitary napkin, or other absorbent article, to be tested is that portion of the absorbent article located at the intersection of the a longitudinally extending centerline 15 and a transversely extending centerline 17.

A 37.5 mm by 37.5 mm test specimen is cut from each of the three product samples. Prior to cutting the test specimens any release paper or packaging material is removed from the product sample and any exposed adhesive, such as garment positioning adhesive, is covered with a non-tacky powder such as talc or the like. The talc should not affect the MCB measurement. The test specimens should not be folded or bent by the test person, and the handling of specimens must be kept to a minimum and to the edges to avoid affecting flexural-resistance properties.

The procedure for the CIRCULAR BEND PROCEDURE is as follows. The specimens are conditioned by leaving them in a room that is 21° C., +/−1° C., and 50%, +/−2.0%, relative humidity for a period of two hours.

A test specimen is centered on the orifice platform below the plunger such that the body facing layer of the test specimen is facing the plunger and the barrier layer of the specimen is facing the platform. The plunger speed is set at 50.0 cm per minute per full stroke length. The indicator zero is checked and adjusted, if necessary. The plunger is actuated. Touching the test specimen during the testing should be avoided. The maximum force reading to the nearest gram is recorded. The above steps are repeated until all of three test specimens have been tested. An average is then taken from the three test values recorded to provide an average MCB stiffness.

Procedure for Measuring Fluid Penetration Time

Absorbent articles according to the present invention can quickly absorb fluid during use. The Fluid Penetration Time test method set forth below measures how quickly an absorbent article absorbs fluid, absorbent articles according to the present invention preferably have Fluid Penetration Time of less than 40 seconds, and more preferably less than 30 seconds, and most preferably less than 15 seconds.

Fluid Penetration Time is measured by placing a sample to be tested under a Fluid Penetration Test orifice plate. The orifice plate consists of a 6.0 inch (15.24 cm) (length) by 3.0 inch (7.62 cm) (width) plate of 0.5 inch (1.27 cm) thick polycarbonate with a 0.5 inch (1.27 cm) diameter circular orifice in its center. The orifice plate is arranged on the product sample to be tested such that the center of the orifice is arranged at the intersection of the longitudinally extending centerline 15 and the transversely extending centerline 17.

A test fluid used in the present test method is made of the following mixture to simulate bodily fluids: 49.5% of 0.9% sodium chloride solution (VWR catalog #VW 3257-7), 49.05% Glycerin (Emery 917), 1% Phenoxyethanol (Clariant Corporation Phenoxetol™) and 0.45% Sodium Chloride (Baker sodium chloride crystal # 9624-05).

A graduated 10 cc syringe containing 1 ml of test fluid is held over the orifice plate such that the exit of the syringe is approximately 3 inches (7.62 cm) above the orifice. The syringe is held horizontally, parallel to the surface of the test plate. The fluid is then expelled from the syringe at a rate that allows the fluid to flow in a stream vertical to the test plate into the orifice and a stop watch is started when the fluid first touches the sample to be tested. The stop watch is stopped when a portion of the surface of the sample first becomes visible above the remaining fluid within the orifice. The elapsed time on the stop watch is the Fluid Penetration Time. The average Fluid Penetration Time (FPT) is calculated from taking the average of three product samples.

Procedure for Measuring Rewet Potential

The three product samples used for the Fluid Penetration Time (FPT) procedure described above are used for the Rewet Potential test described below.

The rewet potential is a measure of the ability of a napkin or other article to hold liquid within its structure when the napkin contains a relatively large quantity of liquid and is subjected to external mechanical pressure. Absorbent articles according to the present invention preferably have a Rewet Potential of less than 0.80 g, more preferably less than 0.65 g, and most preferably less than 0.50 g. The Rewet Potential is determined and defined by the following procedure.

The apparatus for the Rewet Potential test is the same as that set forth above with regard to the FPT test and further includes a quantity of 2 inch×4 inch (5.08 cm×10.16 cm) rectangles of Whatman #1 filter paper (Whatman Inc., Clifton, N.J.) and a weighing machine or balance capable of weighing to an accuracy of +−0.001 g, a standard weight of 2.0 kg having dimensions of 4.0 inches (10.16 cm) (length)× 2.0 (5.08 cm) (width)×1.92 inches (4.87 cm) (height).

For purposes of the test procedure set forth herein, the same three product samples used for the fluid penetration test should be used for the rewet potential test. After the test fluid is applied within the orifice plate in the FPT test described above, and as soon as the cover layer of the napkin first appears through the top surface of the fluid, the plate is remove to start the Rewet Potential Test as described below.

A ten (10) layer stack of the pre-weighed filter paper is placed on and centered over the wetted area and the standard 2.0 kg weight is placed on top of the filter paper. The filter paper and the weight are arranged over the absorbent article such that they are centered over the area to which the fluid was applied. The filter paper and the weight are arranged such that their longer dimensions are aligned with the longitudinal direction of the product. Immediately after placing the paper and weight on the product, the stopwatch is started and after a 15 second interval has elapsed the standard weight and filter paper are quickly removed. The wet weight of the filter paper is measured and recorded to the nearest 0.001 grams. The rewet value is then calculated as the difference in grams between the weight of the wet 10 layers of filter paper and the dry 10 layers of filter paper.

The measurement should have at least three replicates and, if necessary, the weight is wiped clean before each run. The average rewet value (R) is then calculated from the three measured values.

Procedure for Measuring the Thickness of a Sanitary Article

The thickness measurement procedure described below should be conducted on three product samples prior to conducting the MCB test described above after the product samples have been removed from any packaging, any release paper has been removed, and after the product has been powdered with talc or the like. The thickness measurement should be conducted at the intersection of the longitudinally extending centerline 15 and the transversely extending centerline 17 of the absorbent article being tested.

Absorbent articles according to the present invention preferably have a thickness of less than 3.0 mm, more preferably less than 2.0 mm, and most preferably less than 1.5 mm. The procedure for measuring the thickness of an absorbent article is described below.

The apparatus required to measure the thickness of the sanitary napkin is a footed dial (thickness) gauge with stand, available from Ames, with a 2" diameter foot at a pressure of 0.07 psig and a readout accurate to 0.001". A digital type apparatus is preferred. If the sanitary napkin sample is individually folded and wrapped, the sample is unwrapped and carefully flattened by hand. The release paper is removed from the sample and it is repositioned back gently across the positioning adhesive lines so as not to compress the sample, ensuring that the release paper lies flat across the sample. Flaps (if any) are not considered when taking the thickness reading.

The foot of the gauge is raised and the product sample is placed on the anvil such that the foot of the gauge is approximately centered on the location of interest on the product sample. When lowering the foot, care must be taken to prevent the foot dropping onto the sample or undue force being applied. A load of 0.07 p.s.i.g. is applied to the sample and the read out is allowed to stabilize for approximately 5 seconds. The thickness reading is then taken. This procedure is repeated for at three product samples and the average thickness is then calculated.

Procedure for Measuring Vertical Delamination Strength of Absorbent Core Mixture Absorbent core structures 16 according to the present invention surprisingly have superior structural integrity properties despite containing high levels of superabsorbent polymer. The vertical delamination strength (VDS) test set forth below measures the structural integrity properties of a core structure. Absorbent core structures according to the present invention preferably have a VDS of greater than 9 N, more preferably greater than 11 N, and most preferably greater than 13N.

The VDS test is performed as follows. The absorbent article, or material to be tested is first evaluated to determine the location of the superabsorbent/adhesive mixture present in such article. Thereafter, a material sample is taken from such article such that the sample includes the superabsorbent/adhesive mixture and the two directly adjacent materials layers of the article or material to be tested. It may be necessary to remove layers from the absorbent article to isolate the superabsorbent/adhesive mixture and the two directly adjacent materials layers. With regard to the absorbent core structure described above with reference to FIGS. 4-6, the sample tested thus included the first substrate layer 22, second substrate layer 24, and the mixture 26 of superabsorbent polymer and adhesive located between the substrate layers. If the core structure of the particular article being evaluated does not include layers directly adjacent the superabsorbent/adhesive mixture then the material layers of the article that are located directly adjacent the mixture should be employed in the test described below. These layers may include, depending on the particular structure of the article, the cover layer, transfer layer (if present), and/or the barrier layer.

A strip of Spectape ST01 double sided adhesive tape is attached to one surface of the material to be tested. A 50 mm circular sample is cut from the taped portion using an Atom Model SE 20C die press from Associated Pacific Company of Camarillo, Calif. and an appropriately sized cutting die. A test is then performed using a Zwick Model Z005 tensile tester from Zwick/Roell in Ulm, Germany, or the equivalent. In the lower compression portion of the machine, a 50 mm diameter circular platen is attached to the load cell on the moveable crossbeam and a second larger fixed circular platen is mounted to the frame below, opposite the 50 mm moveable platen. The release paper is removed from the taped sample and it is attached to the 50 mm moveable platen using the adhesive surface. A second strip of double-sided tape is applied to the lower platen surface and the release paper is likewise removed. The platens are brought together to a force of 35N, adhering the sample faces to both of them. Then the moveable platen is moved upwards at 75 mm/min, while recording the maximum force applied as the sample delaminates. This maximum force is the vertical delamination force. Examination of the failed sample reveals whether the failure was caused by failure of the sample or if the sample strength exceeded that of one of the taped bonds. If the sample strength exceeded the tape bond, and the maximum measured value exceeds 9N then the measured value should be recorded as the maximum measured value. If the maximum measured value does not exceed 9N due to failure of the tape bond, then the tape should be replaced and the test repeated on the same material sample. The above described process is repeated for a total of three samples and the average VDS is calculated.

Inventive Samples

Inventive Sample 1

A sanitary napkin according to the present invention was constructed to include: (1) a 50 gsm (g/m$^2$) spunlace material including 70% polyester fibers by weight (commercially available as Reliance PET 298G from Reliance Fibers Ltd., Mumbai, India) and 30% polypropylene fibers by weight (commercially available as FV Hywettable T135, wettable polypropylene fibers from ES Fibervisions, Inc., Athens, Ga.); (2) a 45 gsm through air bonded transfer layer including 40% by weight 5.0 denier polypropylene/polyethylene bicomponent fibers and 60% by weight 2.0 denier polypropylene/polyethylene bicomponent fibers; (3) a core including a first 17 gsm wetlaid tissue layer (commercially available as product code 3207 from Cellu Tissue in East Hartford, Conn.), a second 17 gsm wetlaid tissue layer (commercially available as product code 3207 from Cellu Tissue in East Hartford, Conn.), an adhesive/superabsorbent mixture including 80 gsm superabsorbent (Sumitomo SA70, commercially available from Sumitomo Seika Chemicals Co., Ltd., Osaka, Japan) and 6 gsm hotmelt adhesive (HB Fuller NW 1023 hot melt adhesive, commercially available from HB Fuller Company, St. Paul, Minn.), the adhesive/superabsorbent mixture being arranged between the two tissue layers such that mixture extends continuously over 100% of the surface area of the two identically sized tissue layers, the core having a thickness of 0.85 mm and a total surface area of about 5300 mm$^2$; (4) a 0.7 mil polypropylene barrier layer, commercially available under product code XP3471A from Pliant Corporation, Schaumburg, Ill. The cover, transfer layer, core, and barrier were adhered to one another using laminating adhesive commercial available from Fuller Corporation under product code NW-1023ZP.

Inventive Sample 2

A sanitary napkin was constructed according to the present invention to include: (1) a 50 gsm (g/m$^2$) spunlace material including 70% polyester fibers by weight (commercially available as Reliance PET 298G from Reliance Fibers Ltd., Mumbai, India) and 30% polypropylene fibers by weight (commercially available as FV Hywettable T135, wettable polypropylene fibers from ES Fibervisions, Inc., Athens, Ga.); (2) a core including a first 17 gsm wetlaid tissue layer (commercially available as product code 3207 from Cellu Tissue in East Hartford, Conn.), a second 17 gsm wetlaid tissue layer (commercially available as product code 3207 from Cellu Tissue in East Hartford, Conn., an adhesive/superabsorbent mixture including 20 gsm superabsorbent (Sumitomo SA70, commercially available from Sumitomo Seika Chemicals Co., Ltd., Osaka, Japan) and 3 gsm hotmelt adhesive (HB Fuller NW1023 hot melt adhesive, commercially available from HB Fuller Company, St. Paul, Minn.), the adhesive/superabsorbent mixture being arranged between the two tissue layers such that mixture extends continuously over 100% of the surface area of the two identically sized tissue layers, the core having a thickness of 0.73 mm and a total surface area of about 5300 mm$^2$; (3) a 0.7 mil polypropylene barrier layer, commercially available under product code XP3471A from Pliant Corporation, Schaumburg, Ill. The cover, core, and barrier were adhered to one another using laminating adhesive commercial available from Fuller Corporation under product code NW-1023ZP.

|  | MCB (g) | Thickness (mm) | Rewet (g) | FPT (s) | VDS (N) |
|---|---|---|---|---|---|
| Inventive Sample 1 | 77 | 1.9 | 0.3 | 11 | 12 |
| Inventive Sample 2 | 28 | 1.2 | 0.4 | 23 | 14 |

As will be appreciated, one of the advantages achieved by permitting absorbent material formed in accordance with the present invention to equilibrate under pressure as long as 72 hours, such as in roll or bale form, is the desired enhancement of delamination strength, without resort to use of additional adhesive material. Practice of the present invention permits formation of absorbent material having a relatively low ratio of adhesive to superabsorbent polymer, as low as 3.75% or lower, while exhibiting desired absorbency and delamination strength.

The present invention provides enhanced adhesive bonding through efficient distribution of the adhesive material, and effective bonding of the material's components. The formation techniques of the present invention desirably act to ensure efficient adhesive distribution, while the preferred secondary bonding/compaction such as by roll winding or bale compaction enhances component bonding.

The preferred method of secondary bonding such as by roll forming (or other compaction) is believed to be particularly effective because it acts to create surface re-formation of the three-dimensional structure of the material by cold flow of the hot-melt adhesive, thus maintaining the integrity of the superabsorbent polymer. While it is envisioned that lamination of an absorbent core structure could be effected such as by the use of soft foam nip rolls or the like, it is believed that this would limit lamination pressure, with undesirably short service life of such foam rolls. While strong lamination bonding could alternatively be effected at high pressure by the use of flat, steel nip rolls, it is believed that this can undesirably result in caking of the superabsorbent/adhesive mixture and reduce superabsorbent effectiveness.

Thus, the present invention achieves the desired core material performance and integrity while desirably minimizing the use of adhesive. Not only is the adhesive relatively costly, it ordinarily has a negative impact on product absorbency, and can prevent the superabsorbent polymer from swelling as desired. Notably, the present invention provides a highly effective lattice-like structure of the hot-melt adhesive, with enhanced adhesive distribution. Desirably high delamination strength is achieved at relatively low hot-melt adhesive add-on levels by virtue of the secondary bonding that is preferably effected. Very low to no "dusting" of particulate superabsorbent is exhibited at the low hot-melt adhesive add-on levels permitted by practice of the invention. A high apparent density ratio between the material in roll/bale packaging, and the material removed from the packaging, is desirably achieved. Moreover, the absence of any significant change in thickness of the material after additional roll winding or bale compaction suggests that undesired crushing of the superabsorbent material is avoided.

Applications of the absorbent article according to the present invention for sanitary and other health-care uses can be accomplished by any sanitary protection, incontinence, medical and absorbent methods and techniques as are presently or prospectively known to those skilled in the art. Thus, it is intended that the present application cover the modifications and variations of this invention provided that they come within the scope of the appended claims and their equivalents.

I claim:

1. A napkin comprising:
   a liquid permeable cover layer;
   a liquid impermeable barrier layer;
   an absorbent core arranged between the cover layer and barrier layer, the absorbent core comprising a first substrate layer and a second substrate layer, and a mixture of aggregate superabsorbent polymer and a hot melt adhesive between the first substrate layer and the second substrate layer, the hot melt adhesive having a three-dimensional lattice structure formed by a plurality of interconnected lattice segments, wherein the superabsorbent polymer is suspended within the three-dimensional lattice structure, wherein the superabsorbent polymer is present in an amount of between about 50% to about 98% by weight and the hot melt adhesive is present in an amount between about 50% to about 2% by weight, and wherein said mixture is free of fibrous material;
   wherein the mixture extends continuously over a surface area of an adjacent layer in amount greater than 80% of a total surface area of the adjacent layer;
   wherein the mixture has a vertical delamination strength of greater than 9 N;
   wherein the first substrate layer includes a first wetlaid tissue layer;
   wherein the second substrate layer includes a second wetlaid tissue layer; and
   wherein said mixture is applied to the first substrate layer in an amount between 5 gsm and 150 gsm.

2. The napkin according to claim 1, wherein the mixture has a vertical delamination strength of greater than 11 N.

3. The napkin according to claim 2, wherein the mixtures has a vertical delamination strength of greater than 13 N.

4. The napkin according to claim 1, wherein each of the lattice segments has a diameter in the range of about 0.02 mm to about 0.08 mm.

5. The napkin according to claim 1, wherein the mixture extends over a surface area that is greater than 90% of a surface area of an adjacent layer.

6. The napkin according to claim 1, wherein the mixture extends over a surface area that is 100% of a surface area of an adjacent layer.

7. The napkin according to claim 1, wherein an entire portion of the mixture is applied in a continuous layer.

8. The napkin according to claim 1, wherein the mixture extends over a surface area of greater than 2500 mm$^2$.

9. The napkin according to claim 1, wherein the mixture extends over a surface area in the range of about 3000 mm$^2$ to about 15000 mm$^2$.

10. The napkin according to claim 1, wherein the absorbent article has a thickness less than 3.0 mm.

11. The napkin according to claim 10, wherein the absorbent article has a thickness less than 2.0 mm.

12. The napkin according to claim 11, wherein the absorbent article has a thickness less than 1.5 mm.

13. The napkin according to claim 1, wherein the absorbent article has a fluid penetration time of less than 40 seconds.

14. The napkin according to claim 13, wherein the absorbent article has a fluid penetration time of less than 30 seconds.

15. The napkin according to claim 14, wherein the absorbent article has a fluid penetration time of less than 15 seconds.

16. The napkin according to claim 1, wherein the absorbent article has a rewet of less than 0.80 g.

17. The napkin according to claim 16, wherein the absorbent article has a rewet of less than 0.65 g.

18. The napkin according to claim 17, wherein the absorbent article has a rewet of less than 0.50 g.

19. The napkin according to claim 1, wherein the absorbent article has an MCB stiffness of less than 150 g.

20. The napkin according to claim 19, wherein the absorbent article has an MCB stiffness of less than 100 g.

21. The napkin according to claim 20, wherein the absorbent article has an MCB stiffness of less than 50 g.

22. The napkin according to claim 1, wherein the mixture includes 80 gsm superabsorbent and 6gsm hotmelt adhesive.

23. The napkin according to claim 1, wherein the mixture includes 20 gsm superabsorbent and 3 gsm hotmelt adhesive.

24. A napkin comprising:
a liquid permeable cover layer;
a liquid impermeable barrier layer;
an absorbent core arranged between the cover layer and barrier layer, the absorbent core comprising a first substrate layer and a second substrate layer, and a mixture of aggregate superabsorbent polymer and a hot melt adhesive between the first substrate layer and the second substrate layer, the hot melt adhesive having a three-dimensional lattice structure formed by a plurality of interconnected lattice segments, wherein the superabsorbent polymer is suspended within the three-dimensional lattice structure, wherein the superabsorbent polymer is present in an amount between about 50% to about 98% by weight and the hot melt adhesive is present in an amount between about 50% to about 2% by weight, and wherein said mixture is free of fibrous material;
wherein the mixture extends continuously over a surface area of an adjacent layer in an amount greater than 80% of a total surface area of the adjacent layer;
wherein the article has a thickness less than 3.0 mm, a fluid penetration time less than 40seconds and a rewet less than 0.80 g;
wherein the mixture has a vertical delamination strength of greater than 9 N;
wherein the first substrate layer includes a first wetlaid tissue layer;
wherein the second substrate layer includes a second wetlaid tissue layer; and
wherein said mixture is applied to the first substrate layer in an amount between 5 gsm and 150 gsm.

25. The napkin according to claim 24, wherein the mixture has a vertical delamination strength of greater than 11 N.

26. The napkin according to claim 25, wherein the mixture has a vertical delamination strength of greater than 13 N.

27. The napkin according to claim 24, wherein the mixture extends over a surface area that is greater than 90% of a surface area of the adjacent layer.

28. The napkin according to claim 27, wherein the mixture extends over a surface area that is 100% of a surface area of the adjacent layer.

29. The napkin according to claim 24, wherein an entire portion of the mixture is applied in a continuous layer.

30. The napkin according to claim 24, wherein the mixture extends over a surface area of greater than 2500 mm$^2$.

31. The napkin according to claim 30, wherein the mixture extends over a surface area in the range of 3000 mm$^2$ to about 15000 mm$^2$.

32. The napkin according to claim 24, wherein the absorbent article has a thickness less than 2.0 mm.

33. The napkin according to claim 32, wherein the absorbent article has a thickness less than 1.5 mm.

34. The napkin according to claim 24, wherein the absorbent article has a fluid penetration time of less than 30 seconds.

35. The napkin according to claim 34, wherein the absorbent article has a fluid penetration time of less than 15 seconds.

36. The napkin according to claim 24, wherein the absorbent article has a rewet of less than 0.65 g.

37. The napkin according to claim 36, wherein the absorbent article has a rewet of less than 0.50 g.

38. The napkin according to claim 36, wherein the absorbent article has an MCB stiffness of less than 150 g.

39. The napkin according to claim 38, wherein the absorbent article has an MCB stiffness of less than 100 g.

40. The napkin according to claim 39, wherein the absorbent article has an MCB stiffness of less than 50 g.

41. The napkin according to claim 24, wherein each of the lattice segments has a diameter in the range of 0.02 mm to about 0.08 mm.

42. The napkin according to claim 24, wherein said mixture consists of said super absorbent polymer and said adhesive.

43. A napkin comprising:
a liquid permeable cover layer;
a liquid impermeable barrier layer;
an absorbent core arranged between the cover layer and barrier layer, the absorbent core comprising a first substrate layer and a second substrate layer, and a mixture of aggregate superabsorbent polymer and a hot melt adhesive between the first substrate layer and the second substrate layer, the hot melt adhesive having a three-dimensional lattice structure formed by a plurality of interconnected lattice segments, wherein the superabsorbent polymer is suspended within the three-dimensional lattice structure, wherein the superabsorbent polymer is present in an amount of between about 50% to about 98% by weight and the hot melt adhesive is present in an amount between about 50% to about 2% by weight, and wherein said mixture is free of fibrous material;

wherein the mixture extends continuously over a surface area of an adjacent layer in amount greater than 80% of a total surface area of the adjacent layer;

wherein the mixture consists of said super absorbent polymer and said adhesive; wherein the mixture has a vertical delamination strength of greater than 9 N;

wherein the first substrate layer includes a first wetlaid tissue layer;

wherein the second substrate layer includes a second wetlaid tissue layer; and wherein said mixture is applied to the first substrate layer in an amount between 5 gsm and 150 gsm.

44. An absorbent core for a napkin, comprising:

a first substrate layer comprising a wetlaid tissue material;

a second substrate layer comprising a wetlaid tissue material; and an evenly distributed mixture of aggregate superabsorbent polymer and a hot melt adhesive between the first substrate layer and the second substrate layer, the hot melt adhesive having a three-dimensional lattice structure formed by a plurality of interconnected lattice segments;

wherein the superabsorbent polymer is suspended within the three-dimensional lattice structure, wherein the superabsorbent polymer is present in an amount of between about 50% to about 98% by weight and the hot melt adhesive is present in an amount between about 50% to about 2% by weight, wherein the mixture is free of fibrous material, wherein the mixture extends continuously over a surface area of an adjacent layer in amount greater than 80% of a total surface area of the adjacent layer, wherein the mixture has a vertical delamination strength of greater than 9 N, and wherein said mixture is applied to the first substrate layer in an amount between 5 gsm and 150 gsm.

* * * * *